United States Patent [19]

Draheim

[11] 4,234,307
[45] Nov. 18, 1980

[54] OCCLUSAL PLANE ORIENTATION GUIDE

[76] Inventor: Frederick E. Draheim, 4781 Surfwood Dr., Milford, Mich. 48042

[21] Appl. No.: 10,446

[22] Filed: Feb. 8, 1979

[51] Int. Cl.³ ............................................. A61C 19/04
[52] U.S. Cl. ...................................................... 433/73
[58] Field of Search ......................... 32/20, 21, 19, 32; 433/73

[56] References Cited

U.S. PATENT DOCUMENTS

| | | | |
|---|---|---|---|
| 2,874,469 | 2/1959 | Federiol | 32/20 |
| 4,059,899 | 11/1977 | Dyal | 32/32 |

Primary Examiner—Robert Peshock
Attorney, Agent, or Firm—Krass & Young

[57] ABSTRACT

An orientation guide for adjustment of the occlusal plane of a set of dentures relative to the cranial anatomy of a patient includes a flat plate having a curved bite piece and a pair of laterally and distally extending wing sections projecting in opposed directions from the proximal end of the bite piece. A pair of wire guide extensions are supported in the distal ends of each of the wings and include end sections adjustably supported parallel to and above the wings and adapted to be aligned with the patient's ala-tragal line to facilitate parallelism of the occlusal plane to that line.

2 Claims, 2 Drawing Figures

OCCLUSAL PLANE ORIENTATION GUIDE

BACKGROUND OF THE INVENTION

1. Field of the Invention

This invention relates to an occlusal plane orientation guide adapted for use during adjustment of a denture to insure proper alignment of the denture relative to the patient's cranial anatomy.

2. Prior Art

The occlusal plane of artificial dentures must bear a particular relationship to the cranial anatomy of the wearer to insure their proper function and appearance. This orientation is generally expressed in terms of the position of an imaginary occlusal plane of the dentures which theoretically touches the incisal edges of the incisors and tips of the occluding surfaces of the posterior teeth. This is not a plane in the true sense of the word, in some cases, but may represent the mean of the curvature of this surface. It is generally desirable that this plane extend parallel to a line drawn from the tragus of the ear to the ala of the nose to insure proper function and appearance of the dentures. The occlusal plane should additionally extend parallel to the interpupillary line. If the occlusal plane as it pertains to the lower denture is raised or lowered too much, the patient may experience difficulty in removing the food from the occlusal table, and therefore tend to dislodge the lower denture, or bite the lateral borders of the tongue.

A popular device for use in establishing proper orientation of the occlusal plane has consisted of a thin, flat plate having a central curved bite piece and a pair of laterally and distally extending wings projecting from the proximal end of the bite piece and adapted to overline the exteriors of the opposite buccinator muscle complexes (cheeks) of the patient. During fitting of the denture the bite piece is oriented on the maxillary denture so that the plate is on the occlusal plane and the wax denture bite block is adjusted so that the wings of the plate extend parallel to the ala-tragus line. This is usually done by either drawing the ala-tragus line on the patient's face using a straight edge and a grease pencil or some similar technique. This alignment process is awkward and time consuming and frequently results in a misalignment of the denture. It is therefore a primary object of the present invention to provide an improved occlusal plane orienter which simplifies the process of achieving alignment of the dentures with the cranial anatomy and insures proper alignment.

SUMMARY OF THE INVENTION

The present invention is broadly directed toward an occlusal plane orientation guide consisting of a flat plate contoured to have a central curved bite piece with a pair of laterally and distally extending wings projecting in opposed directions from the proximal end of the bite piece, and further having guide extensions adjustably supported in the distal end of each of the wings. The guide extensions include straight end sections extending parallel to the wing. The separations of these end sections from their wings and the rotational orientation of the end sections in the plane of the wings may be adjusted so that the end sections may be aligned along the ala-tragus line of the patient when the bite piece is supported against the occlusal surface of the denture being adjusted. This insures parallelism between the occlusal plane and the ala-tragus line.

In a preferred embodiment of the invention, which will be subsequently disclosed in detail, the adjustable extensions take the form of lengths of wire. Each wire is bent so as to form the first section which is adapted to make a snug sliding fit within an aperture formed through the plate wings as their distal ends. This first section projects normally to the plane of the plate. At its upper end the wire is bent at a right angle to form an intermediate section extending parallel to the plate and projecting distally, toward the patient's ear. The far end of this intermediate section is rebent through 180° to form an end section which projects parallel to the plate and has a sufficient length to extend between the ear and the nose of the patient. This end section may be curved slightly to increase its approximation to the cheek surface and can be readily adjusted in both rotational orientation in the plane of the plate and vertically by adjustment of the first wire section within the plate aperture. The end section may thus be vertically adjusted to lie along the ala-tragus line and the occlusal plane altered to be parallel. Other objects, advantages and applications of the present invention will be made apparent by the following detailed description of a preferred embodiment of the invention. The description makes reference to the accompanying drawings, in which:

Figure 1:
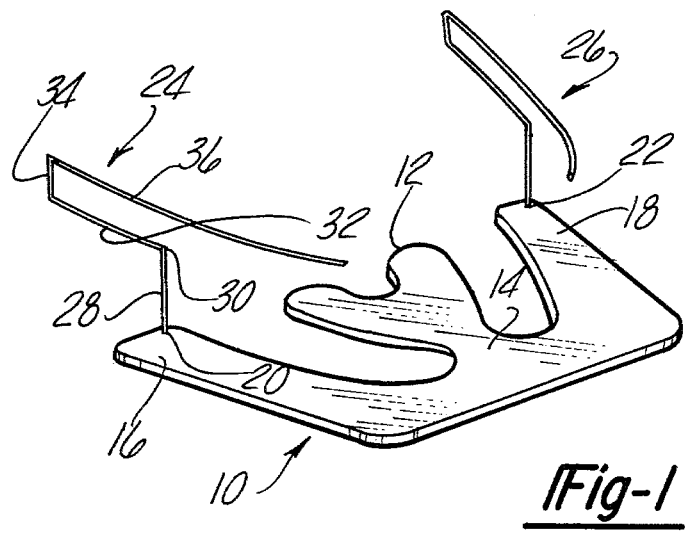
FIG. 1 is a perspective view of a preferred embodiment of my plate.

Referring to the drawings, the occlusal plane orientation plate of the present invention includes a flat planar section generally indicated at 10, preferably formed of an acrylic plastic or the like. The plate 10 includes a conventionally curved bite piece 12 connected at its proximally extending end 14 to a pair of laterally and distally extending wings 16 and 18 which project in opposed directions.

Figure 2:
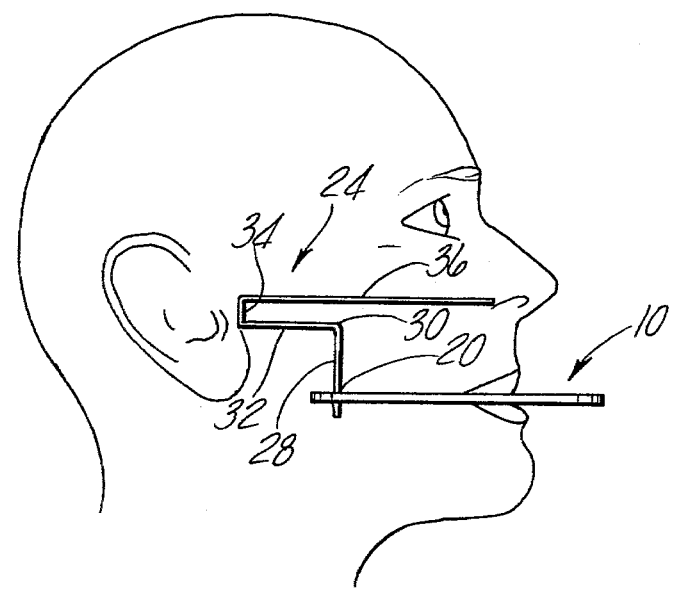
FIG. 2 is a perspective view of a plate of the present invention with the bite piece engaged by a set of dentures to illustrate its method of use.

As is shown in FIG. 2, when the bite piece is supported on the occlusal rim of the maxillary denture being fitted, the plate 10 lies on the occlusal plane with the wings 16 and 18 extending over the exteriors of the opposite cheeks of the patient with the distal ends of the wings terminating forward of and below the patient's ears.

As heretofor described, the plate 10 is similar to the occlusal plane orientation plates of the prior art.

Small diameter circular apertures 20 and 22 are formed laterally through the material of the plate adjacent the distal ends of the plate wings 16 and 18 respectively. These apertures may be approximately 0.030–0.040 inch in diameter and drilled 90° to the plate surface. A pair of wire extension guides generally indicated at 24 and 26 are supported in the apertures 20 and 22 respectively. The wire guides are substantially identical, except for their curvature, and identical numerical designations will be used on each.

Each extension guide is formed by steel wire, preferably stainless steel, having a diameter substantially equal to the apertures 20 and 22, or approximately 0.030–0.040 inch. Each guide has a first, relatively straight section 28 which is adapted to be inserted into one of the apertures 20 or 22 and to form a snug sliding fit with respect thereto. This fit allows the end section 28 to be adjusted within the aperture both vertically and rotationally and to remain in its adjusted position in the absence of manual pressure applied to the guide. In the preferred embodiment of the invention the end section 28 will have a length of approximately 1½ inches. A 90° bend 30 is formed at one end of the first section to form a second section 32 which extends substantially normally to the plate 10 when the end section 28 is supported within one of the apertures in the plate. At the other end of the second section 32 a 180° U-shaped bend 34 is formed to create a third, end section 36 which extends parallel to the plate 10 when the end 28 is inserted within the plate. The third section may have a slight gradual curvature in the plane of the plate so as to approximate the curvature of the patient's cheek. The curvature of the two guide extensions 24 and 26 will be in opposite directions so that their concave sections oppose one another.

In use, the bite piece 12 on the plate 10 is held against the maxillary denture to be fitted to the patient so that the plate 10 lies on the tentative occlusal plane of the denture. The end sections 28 of the wire guide extensions are then raised or lowered within their supporting apertures, adjusting the spacing of the end sections 36 from the plate to allow the sections 36 to be aligned with the ala-tragus lines of the patient. The sections 36 may also be rotated in planes parallel to the plate by rotation of the end sections 28 within their supporting apertures. When the sections 36 are in alignment with the two ala-tragus lines of the patient the plate 10 necessarily extends parallel to the ala-tragus lines. Adjustments of the wax bit blocks may be made to achieve this orientation.

The occlusal orientation guide of the present invention is accordingly simple to use and results in a high degree of accuracy of occlusal plane orientation.

The embodiments of the invention in which an exclusive property or privilege is claimed are defined as follows:

1. A guide for use in orienting the occlusal plane of a denture set to the cranial anatomy of a patient comprising:

a thin planar plate having a central curved bite piece and a pair of laterally and distally extending wings projecting in opposed directions from the proximal end of the bite piece and adapted to extend in the occlusal plane over the opposed cheeks of the patient when the bite piece is engaged by the opposed denture sections;

and a pair of guide wire extensions, each extension having one end section slidably supported within an aperture in the wing formed laterally to the plane of the plane and an opposite end section projecting parallel to the wings of the plates whereby the parallel end sections of the extensions may be aligned with the ala-tragus line or the patient by sliding and rotation of the first end sections in their supporting wing apertures to allow proper orientation of the occlusal plane with respect thereto.

2. The occlusal plane orientation guide of claim 1 wherein the first end section of each of the guide extensions are connected to the opposite section of the guide extension by an intermediate section extending parallel to the opposite section and adapted to project distally so that one end of the opposite section begins distally relative to the distal ends of the wings.

* * * * *

UNITED STATES PATENT AND TRADEMARK OFFICE
CERTIFICATE OF CORRECTION

PATENT NO. : 4,234,307
DATED : 11/18/80
INVENTOR(S) : Frederick E. Draheim

It is certified that error appears in the above–identified patent and that said Letters Patent are hereby corrected as shown below:

Column 4, line 20 (Claim 1), "or" should be --of--.

Signed and Sealed this

Twenty-sixth Day of May 1981

[SEAL]

Attest:

RENE D. TEGTMEYER

Attesting Officer     Acting Commissioner of Patents and Trademarks